United States Patent
Kohlhammer et al.

(10) Patent No.: US 10,932,949 B2
(45) Date of Patent: Mar. 2, 2021

(54) CONTROL DEVICE FOR A PHACOEMULSIFICATION SYSTEM AND PHACOEMULSIFICATION SYSTEM COMPRISING SUCH A CONTROL DEVICE

(71) Applicant: Carl Zeiss Meditec AG, Jena (DE)

(72) Inventors: Susanne Kohlhammer, Blaustein (DE); Martin Fanenbruck, Oberkochen (DE); Peter Langheinrich, Oberkochen (DE)

(73) Assignee: Carl Zeiss Meditec AG, Jena (DE)

( * ) Notice: Subject to any disclaimer, the term of this patent is extended or adjusted under 35 U.S.C. 154(b) by 799 days.

(21) Appl. No.: 15/793,492

(22) Filed: Oct. 25, 2017

(65) Prior Publication Data

US 2018/0042770 A1    Feb. 15, 2018

Related U.S. Application Data

(63) Continuation of application No. PCT/EP2016/057561, filed on Apr. 7, 2016.

(30) Foreign Application Priority Data

Apr. 25, 2015 (DE) ............ 10 2015 005 331.0

(51) Int. Cl.
*A61F 9/007* (2006.01)
*A61F 9/008* (2006.01)
*A61B 17/00* (2006.01)

(52) U.S. Cl.
CPC ...... *A61F 9/00745* (2013.01); *A61B 2017/00181* (2013.01); *A61F 9/00736* (2013.01); *A61F 2009/00887* (2013.01)

(58) Field of Classification Search
CPC .................. A61F 9/00736; A61F 2009/00887
See application file for complete search history.

(56) References Cited

U.S. PATENT DOCUMENTS 5,098,426 A * 3/1992 Sklar ............... A61F 9/008
                                               606/5
6,506,176 B1 * 1/2003 Mittelstein ......... A61F 9/013
                                               604/22
(Continued)

FOREIGN PATENT DOCUMENTS

DE    10 2008 046 687 A1    3/2009
DE    10 2011 114 584 B3    5/2012
(Continued)

OTHER PUBLICATIONS

International Search Report received in international application PCT/EP2016/057561 from which this application claims priority and English-language translation thereof, dated Jun. 9, 2016.
(Continued)

*Primary Examiner* — Ronald D Hartman, Jr.
(74) *Attorney, Agent, or Firm* — Falk Ewers; Ewers IP Law PLLC

(57) ABSTRACT

A control apparatus for a phacoemulsification system is disclosed. The control apparatus is configured to supply electrical energy to an actuator for a phaco needle during a plurality of time intervals, wherein the time intervals includes a first time interval, in which electrical energy for pulses with a constant maximum amplitude is supplied, a second time interval following the first time interval, wherein electrical energy with a value equal to zero is supplied, and a third time interval following the second time interval, wherein the third time interval has a first time duration in which electrical energy for pulses which have a lower constant amplitude than the maximum amplitude during the first time interval is supplied.

9 Claims, 2 Drawing Sheets

(56) References Cited

U.S. PATENT DOCUMENTS

| | | | |
|---|---|---|---|
| 8,277,462 B2 | 10/2012 | Heymann et al. | |
| 2004/0092921 A1* | 5/2004 | Kadziauskas | B06B 1/023 606/27 |
| 2004/0116911 A1* | 6/2004 | Kadziauskas | A61F 9/00745 606/6 |
| 2005/0209560 A1* | 9/2005 | Boukhny | A61F 9/00745 604/118 |
| 2005/0209621 A1* | 9/2005 | Gordon | A61F 9/00745 606/169 |
| 2007/0056596 A1* | 3/2007 | Fanney | B06B 1/0215 128/898 |
| 2007/0078379 A1 | 4/2007 | Boukhny et al. | |
| 2008/0319374 A1* | 12/2008 | Zacharias | A61M 1/0035 604/22 |
| 2009/0118663 A1* | 5/2009 | Rockley | A61F 9/008 604/20 |
| 2010/0268388 A1 | 10/2010 | Boukhny et al. | |
| 2014/0214024 A1 | 7/2014 | Eichler | |
| 2015/0202081 A1 | 7/2015 | Eichler | |

FOREIGN PATENT DOCUMENTS

| | | |
|---|---|---|
| DE | 10 2012 018 982 A1 | 3/2014 |
| EP | 1 765 190 B1 | 7/2008 |
| WO | 2005/092047 A2 | 10/2005 |

OTHER PUBLICATIONS

International Preliminary Report on Patentability received in international application PCT/EP2016/057561 from which this application claims priority, dated Jan. 11, 2018.

* cited by examiner

CONTROL DEVICE FOR A PHACOEMULSIFICATION SYSTEM AND PHACOEMULSIFICATION SYSTEM COMPRISING SUCH A CONTROL DEVICE

CROSS REFERENCE TO RELATED APPLICATIONS

This application is a continuation application of International Application No. PCT/EP2016/057561 filed on Apr. 7, 2016, and claims priority to German patent application DE 10 2015 005 331.0 filed on Apr. 25, 2015, both of which are hereby incorporated by reference in their entireties.

TECHNICAL FIELD

The disclosure relates to a control apparatus for a phacoemulsification system and a phacoemulsification system having such a control apparatus.

BACKGROUND

There are multiple surgical techniques for treating a clouding of the eye lens, which is referred to as a cataract in medicine. The most widespread technique is phacoemulsification, in which a thin hollow needle (phaco needle) is introduced into the eye lens and induced to vibrate by ultrasound. In its immediate surroundings, the vibrating hollow needle emulsifies the eye lens such that the resulting lens particles can be aspirated through the hollow needle and a line connected thereto, which together form an aspiration line that is driven by a pump. In the process, an irrigation fluid is supplied. When the eye lens has been completely emulsified and removed, a new artificial lens can be inserted into the empty capsular bag, and so a patient treated in this way can re-attain good vision.

To obtain complete emulsification of the eye lens in the shortest possible time and, as a consequence, an operation duration that is as short as possible for the patient, it is expedient to move the hollow needle with the greatest possible longitudinal amplitudes. This can be carried out by supplying electrical energy to an actuator in the form of piezoelectric elements such that the actuator, with the hollow needle coupled thereto, vibrates in the region of the resonant frequency.

When electrical energy is supplied for a sufficiently long period of time to the piezoelectric elements during phacoemulsification, it is not only the piezoceramic elements that heat up. The region around the hollow needle that is coupled to the piezoelectric elements also heats up to such an extent that the cornea which is pierced for the phacoemulsification may burn in the surroundings of the hollow needle. Such injury should be avoided at all costs. In this respect, there is a conflict between supplying as much energy as possible for the purposes of emulsifying an eye lens but, in the process, not causing excessive heating up of the cornea.

US 2007/0078379 A1 proposes a multiplicity of pulses, by which the phaco needle can be moved. The pulses increases linearly from a low amplitude to a higher amplitude and decrease linearly from the higher amplitude to the lower amplitude. This should represent an improvement over the previously known rectangular pulses since, in the case of rectangular pulses, lens particles would not be held well on the phaco needle and even pushed away from the phaco needle, and so only very poor emulsification would be possible. A large amount of energy had to be supplied to the phaco needle moved by the rectangular pulses so that, nevertheless, a sufficient emulsification could take place. This means nothing other than the rectangular pulses would need to have a very high amplitude; however, excessive heat would be introduced into the tissue as a result thereof, and this should be avoided. Moreover, cavitation effects, i.e., imploding bubbles, would be produced by rectangular pulses, as a result of which unwanted heat and unwanted additional forces would likewise be introduced into the tissue.

US 2010/0268388 A1 describes a method for controlling a surgical system on the basis of an irrigation volume flow. To this end, the temperature of the eye is determined during the operation, wherein the energy supplied to the phaco needle is reduced if, on account of the determined temperature, overheating of the tissue is to be expected. The energy is reduced in such a way that the height of the rectangular pulses, i.e., their amplitude, is reduced.

SUMMARY

It is an object of the disclosure to develop a control apparatus for a phacoemulsification system and a phacoemulsification system having such a control apparatus, in which, with little control outlay, the emulsification of an eye lens can be achieved in a short period of time, with a high degree of effectiveness, and with a low risk of burning the cornea.

This object is achieved by the subject matter disclosed herein.

The control apparatus for a phacoemulsification system is configured to supply electrical energy to an actuator for a phaco needle during a plurality of time intervals, wherein the time intervals comprise:
  a first time interval, in which electrical energy for pulses which have a constant maximum amplitude is supplied,
  a second time interval following the first time interval, wherein electrical energy with a value equal to zero is supplied during the second time interval, and
  a third time interval following the second time interval, wherein the third time interval has a first time duration in which electrical energy for pulses which have a lower constant amplitude than the maximum amplitude during the first time interval is supplied,
  i) wherein the first time duration is followed by a second time duration in which pulses having an amplitude reaching a constant magnitude equal to more than 0% and less than 10% of the maximum amplitude are applied, and
  ii) wherein the first time duration of the third time interval is shorter than the first time interval.

As a consequence, the control apparatus according to an aspect of the disclosure is configured in such a way that relatively large amounts of energy are introduced into the eye lens with a maximum amplitude during the first time interval to be able to start effective emulsification of the eye lens. Then, by way of the second time interval, this is followed by a pause in which no energy is supplied such that the phaco needle and the cornea surrounding the latter may cool. However, this cooling is not allowed for such a long time that a temperature like at the start of the first time interval is reached, as this would require a relatively long time and would not allow the phacoemulsification to be carried out quickly enough. Therefore, the control apparatus is configured such that a third time interval with a first time duration follows the expiry of the second time interval, electrical energy being supplied during the first time duration to the actuator for pulses which have a lower amplitude than those during the first time interval. The lower amplitude causes less energy being supplied than in the first time interval, and so although phacoemulsification takes place, this happens with a lower intensity. The cooling can continue during the first time duration. The energy supplied during the second time duration that follows the first time duration is so low that there no longer is emulsification, as a result of which cooling still can continue. However, the energy supplied during the second time duration in the third time interval does not have the magnitude of zero, and so the actuator continues to vibrate. This is advantageous because the vibration behavior of the actuator in the form of piezoelectric elements can be evaluated during the entire third time interval. By way of example, it is possible to check the position of the resonant frequency or an occlusion state on the phaco needle. If a repetition of the first time interval to the third time interval follows the third time interval, the vibration of the actuator again can be effectuated at a newly set resonant frequency.

The inventors have determined that the use of the control apparatus according to the disclosure renders it possible to carry out an effective emulsification of the eye lens within a short period of time while, at the same time, there is a low thermal load on the tissue surrounding the phaco needle and, in particular, on the cornea. The inventors additionally have determined the particularly advantageous property that the produced lens particles can be suctioned well into the aspiration line by using the control apparatus according to the disclosure due to the aforementioned time intervals, even though the lens particles are pushed away from the needle tip by the hollow needle that is vibrating in the longitudinal direction at the same time. Here, in particular, the second time interval, in which no energy is supplied to the actuator of the phaco needle, is important. Further, the inventors have observed that, by using the control apparatus according to the disclosure, a contact between the longitudinally vibrating tip of the hollow needle and the eye lens still is relatively good in the case of a relatively hard eye lens due to the aforementioned time intervals, and so good emulsification is achieved. As a consequence, the lens particles are held well on the needle by using the control apparatus according to the disclosure, wherein, overall, an emulsification of the eye lens is possible with a high degree of efficiency and with little risk of burning the cornea.

According to an exemplary embodiment of the disclosure, the length of the first time interval is predetermined, wherein only the length of the third time interval is modifiable by repositioning a foot pedal. As a result, sufficient energy is supplied to the eye lens during the entire first time interval, wherein the time for cooling in the third time interval can be adapted to the respective situation during an ophthalmic surgical operation. This decision as to how the foot pedal is actuated to set the time for the third time interval accordingly is made by the surgeon on the basis of his or her experience and observations during the operation. Thus, there is no control on account of a measured temperature on the phaco needle. There is also no control on account of a load on the phaco needle due to a lens particle during the operation. There is also no image processing of the surroundings of the distal end of the phaco needle. Moreover, there is no automatic closed-loop control of the pulse modes on account of a change in a surgical parameter. Such approaches are deliberately dispensed with in the control apparatus according to the disclosure. By way of example, only a length of the first time interval and, typically, also a length of the second time interval are preset on a graphical user interface, wherein the surgeon only changes the length of the third time interval by means of a foot pedal.

According to a further exemplary embodiment of the disclosure, the length of the third time interval and, typically, also of the second time interval are predetermined, for example by setting these on a graphical user interface, wherein only the length of the first time interval is modifiable by repositioning a foot pedal. Hence, the surgeon can achieve a relatively low overall energy input into the eye lens.

Typically, the amplitude of the pulses in the first time duration of the third time interval is adjustable within a range of 40% to 70% of the maximum amplitude from the first time interval. What this achieves is that phacoemulsification still takes place, but only with a lower amount of energy to avoid further strong heating of the surroundings of the phaco needle.

According to an exemplary embodiment of the disclosure, the third time interval has a first time duration and a second time duration and, directly following this, a third time duration and a fourth time duration, wherein electrical energy for pulses which have a lower constant amplitude than during the first time interval is supplied during the third time duration and pulses with an amplitude reaching a constant magnitude equal to more than 0% and less than 10% of the maximum amplitude are applied during the fourth time duration. Typically, the amplitude of the pulses in the third time duration of the third time interval is adjustable within a range of 40% to 70% of the maximum amplitude from the first time interval. Hence, further cooling in the third time interval is facilitated, while, nevertheless, a sufficient degree of emulsification is still possible. Additionally, the vibration behavior of the actuator can be evaluated during the entire third time interval.

Typically, the ratio of the third time interval to the first time interval is adjustable in a range from 0.5 to 2, preferably in a range from 0.5 to 1, by repositioning the foot pedal. As a consequence, the third time interval is at least half as long and at most twice as long as the first time interval.

According to a further exemplary embodiment of the disclosure, the pulses during the third time duration have a lower constant amplitude than during the first time duration. Typically, the amplitude in the third time duration lies within a range of 15% to 35% of the maximum amplitude from the first time interval. Hence, an even lower energy supply during the third time duration is ensured, and so even more reliable cooling of the surroundings of the phaco needle is possible.

BRIEF DESCRIPTION OF THE DRAWINGS

Further advantages and features of the disclosure are explained with reference to the following drawings, in which.

DESCRIPTION OF EXEMPLARY EMBODIMENTS

Figure 1:
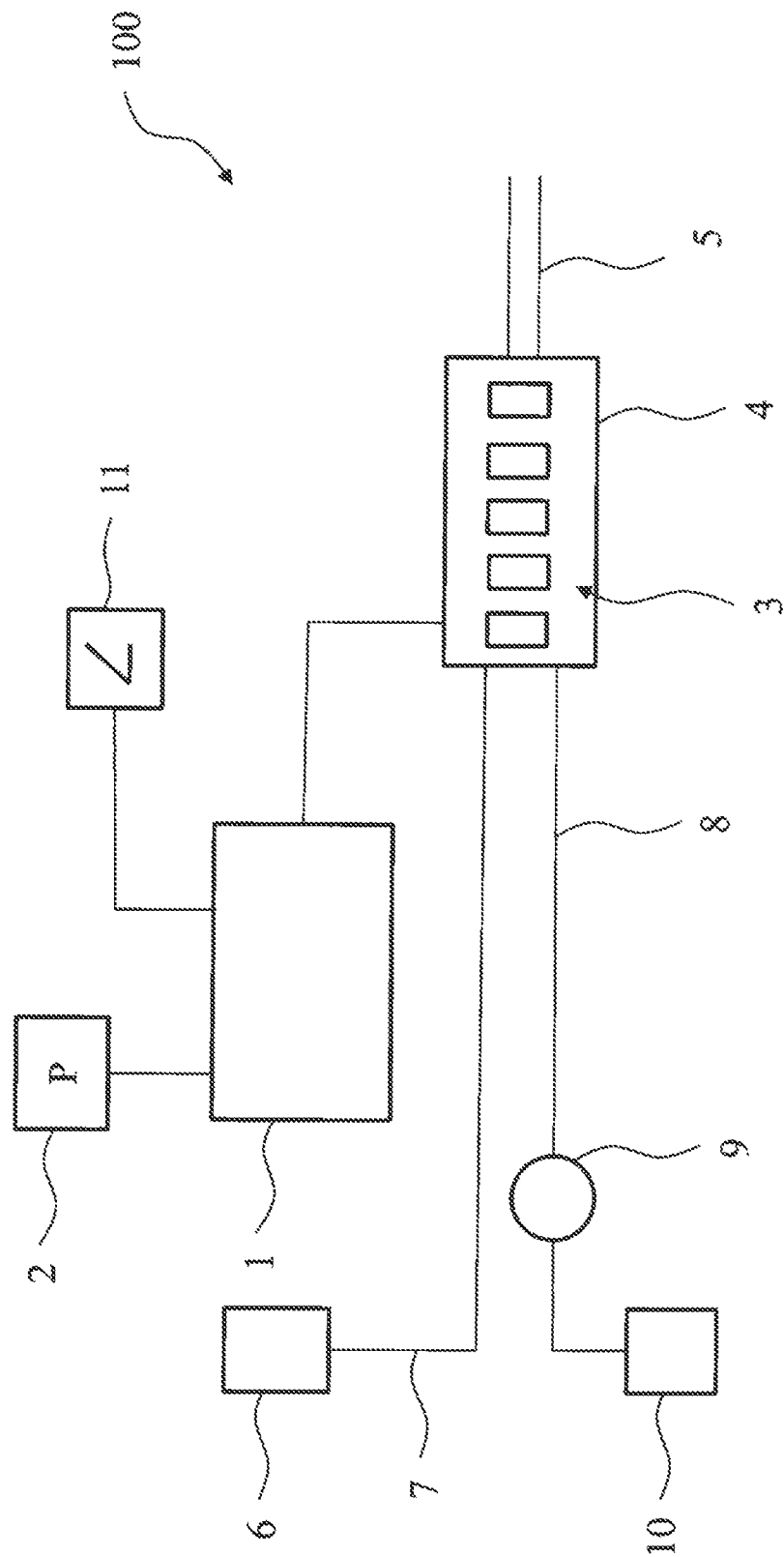
FIG. 1 shows a schematic illustration of a phacoemulsification system.

FIG. 1 shows a schematic illustration of a phacoemulsification system 100 according to the disclosure. The phacoemulsification system 100 has a control apparatus 1, which is coupled to an energy supply 2. The energy supply 2 is required to supply an actuator 3, e.g., made of piezoelectric elements, in a phaco handpiece 4 with energy such that a phaco needle 5 that is coupled to the actuator 3 can carry out a longitudinal vibration. In the region of a distal end of the phaco needle 5, an irrigation fluid 6 is supplied through an irrigation line 7, the irrigation fluid, by means of an aspiration line 8, being transported together with emulsified lens particles to an aspiration fluid container 10 by an aspiration pump 9. The control apparatus 1 is further coupled to a foot pedal 11 such that, depending on the position of the foot pedal 11, the actuator 3 of the phaco handpiece can be actuated by the control apparatus 1.

Figure 2:
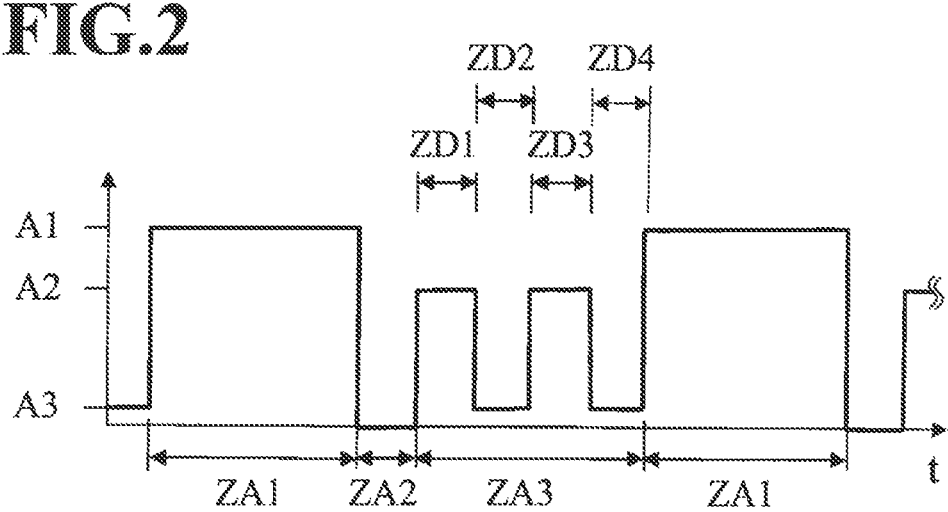
FIG. 2 shows a schematic illustration of a pulse profile as a function of time according to a first exemplary embodiment of the control apparatus.

FIG. 2 shows a schematic illustration of a pulse profile as a function of time according to a first exemplary embodiment of the control apparatus 1. The actuator 3 of the handpiece 4 is supplied with electrical energy during a first time interval ZA1 such that the phaco needle 5 is caused to vibrate with the constant maximum amplitude A1. After the first time interval ZA1 has expired, there is a second time interval ZA2, in which electrical energy with the value of zero is supplied to the actuator 3 by the control apparatus 1, such that the amplitude of the phaco needle 5 has a magnitude of zero. On account of completely dispensing with a supply of energy in this second time interval ZA2, there is a maximum possible cooling of the tissue in the surroundings of the phaco needle.

The second time interval ZA2 is followed by a third time interval ZA3 which, in this exemplary embodiment, comprises a first time duration ZD1, a second time duration ZD2, a third time duration ZD3, and a fourth time duration ZD4. Electrical energy is supplied by the energy supply 2 to the actuator 3 and, as a consequence, to the phaco needle 5 during the first time duration ZD1 and during the third time duration ZD3 such that pulses having a constant amplitude A2 are applied. In this exemplary embodiment, the amplitude A2 is approximately 70% of the maximum amplitude A1 and hence smaller than the maximum amplitude A1 during the first time interval ZA1.

During the second time duration ZD2 and during the fourth time duration ZD4, pulses having a constant amplitude A3 reaching a magnitude equal to more than 0% and less than 10% of the maximum amplitude A1 are applied. Hence, there is no emulsification of the eye lens during the second time duration ZD2 and during the fourth time duration ZD4, and so the surroundings of the phaco needle can cool down. Consequently, there is a movement of the phaco needle during the first time interval ZA1 and during the third time interval ZA3, as a result of which the current that is required for the actuator operation and the voltage drop can be ascertained in each case. This is advantageous because, as a consequence, it becomes possible, e.g., to evaluate the occlusion state of the phaco needle during this time. By contrast, no current supplied to the actuators and hence also no voltage drop at the actuators are ascertained or an occlusion state of the phaco needle is captured during the second time interval ZA2. The second time interval ZA2 only serves to facilitate maximum cooling. Since the electrical energy supplied to the actuator during the second time interval has a value equal to zero, no current is supplied to the actuators either, and so there is no need to evaluate the current and a voltage drop over the actuators.

After the third time interval ZA3, the pulse profile repeats itself from the first time interval ZA1 to the third time interval ZA3, as a result of which effective emulsification is achieved, which, however, is very sparing with regard to a temperature increase in the region of the cornea.

Figure 3:
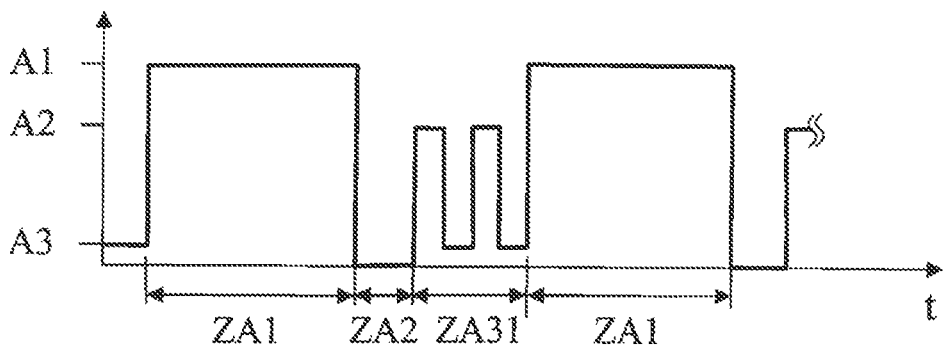
FIG. 3 shows a schematic illustration of a pulse profile as a function of time according to a second exemplary embodiment of the control apparatus.

FIG. 3 illustrates a pulse profile according to a second exemplary embodiment of the control apparatus. The first time interval ZA1 and the second time interval ZA2 are unchanged in comparison with the illustration in FIG. 1. However, the third time interval ZA31 is shorter than the third time interval ZA3 according to FIG. 2. This shortening of the third time interval is achieved by an appropriate position of the foot pedal 11. The control apparatus can be configured in such a way that the third time interval successively reduces from the length ZA3 to ZA31 as the foot pedal 11 is pressed down further. Hence, it is possible to supply slightly more energy into the eye lens in the case of a relatively hard eye lens.

Figure 4:
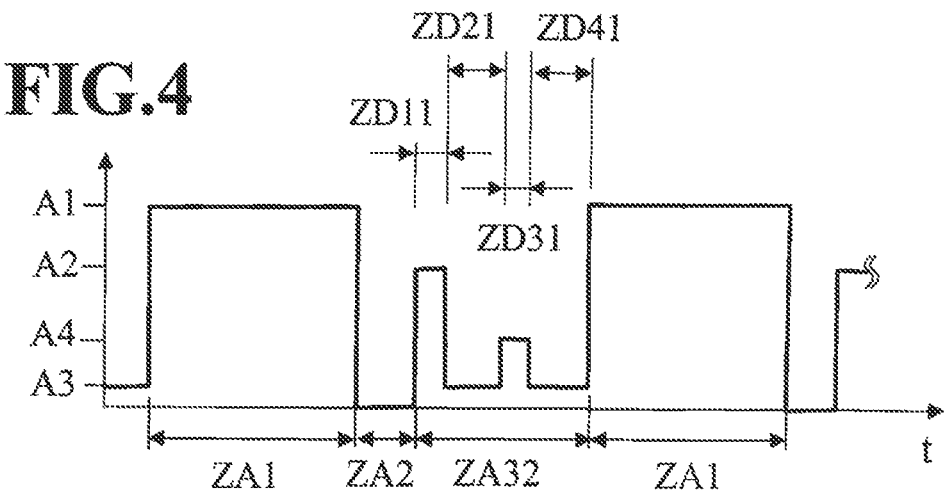
FIG. 4 shows a schematic illustration of a pulse profile as a function of time according to a third exemplary embodiment of the control apparatus according to the disclosure.

FIG. 4 shows a schematic illustration of a pulse profile as a function of time according to a third exemplary embodiment of the control apparatus 1 according to the disclosure. In terms of the first time interval ZA1 and the second time interval ZA2, the pulse profile is identical to the pulse profile illustrated in FIG. 1. However, the pulse profile in the third time interval ZA32 differs from the third time interval ZA3 in that the pulses are applied during different time durations ZD11, ZD21, ZD31, and ZD41. The pulses during the second time duration ZD21 and the fourth time duration ZD41 have the same length as the time interval ZA2, in which no pulses are applied. Moreover, the pulses during the third time duration ZD31 have a constant amplitude A4. The amplitude A4 is lower than the amplitude A1 and the amplitude A2, but higher than the amplitude A3. Hence, the height of the amplitudes is stepped from A1 to A2 to A4 to A3, bringing about a very soft reduction in the vibration energy supplied into the eye lens. Hence, on account of good cooling during the emulsification process, a good compromise is achieved between an emulsification with a high degree of effectiveness within a short period of time and a lower risk of burning the cornea.

The term "comprising" (and its grammatical variations) as used herein is used in the inclusive sense of "having" or "including" and not in the exclusive sense of "consisting only of." The terms "a" and "the" as used herein are understood to encompass the plural as well as the singular.

All publications, patents and patent applications cited in this specification are herein incorporated by reference, and for any and all purposes, as if each individual publication, patent or patent application were specifically and individually indicated to be incorporated by reference. In the case of inconsistencies, the present disclosure will prevail.

What is claimed is:

1. A control apparatus for a phacoemulsification system, wherein the control apparatus is configured to supply electrical energy to an actuator for a phaco needle during a plurality of time intervals, wherein the time intervals comprise:
   a first time interval, in which electrical energy for pulses for a phacoemulsification is supplied, wherein the pulses have a constant maximum amplitude,
   a second time interval following the first time interval, wherein electrical energy with a value equal to zero is supplied during the second time interval, and
   a third time interval following the second time interval, wherein the third time interval has a first time duration in which electrical energy for pulses for a phacoemulsification is supplied, and wherein the pulses have a lower constant amplitude than the maximum amplitude during the first time interval, wherein the first time duration is followed by a second time duration in which pulses having an amplitude reaching a constant magnitude equal to more than 0% and less than 10% of the maximum amplitude are applied, such that there is no phacoemulsification during the second time duration, wherein the first time duration of the third time interval is shorter than the first time interval.

2. The control apparatus as claimed in claim 1, wherein the length of the first time interval is predetermined and only the length of the third time interval is modifiable by repositioning a foot pedal.

3. The control apparatus as claimed in claim 1, wherein the length of the third time interval is predetermined and only the length of the first time interval is modifiable by repositioning a foot pedal.

4. The control apparatus as claimed in claim 1, wherein the amplitude of the pulses during the first time duration of the third time interval is adjustable within a range of 40% to 70% of the maximum amplitude of the first time interval.

5. The control apparatus as claimed in claim 1, wherein the third time interval has a first time duration and a second time duration and, directly following the second time duration, a third time duration and a fourth time duration, wherein electrical energy for pulses which have a lower constant amplitude than during the first time interval is supplied during the third time duration and pulses with an amplitude reaching a constant magnitude equal to more than 0% and less than 10% of the maximum amplitude are applied during the fourth time duration.

6. The control apparatus as claimed in claim 5, wherein the pulses during the third time duration have a lower constant amplitude than during the first time duration.

7. The control apparatus as claimed in claim 1, wherein the ratio of the third time interval to the first time interval is adjustable in a range from 0.5 to 2 by repositioning the foot pedal.

8. The control apparatus as claimed in claim 7, wherein the ratio of the third time interval to the first time interval is adjustable in the range from 0.5 to 1.

9. A phacoemulsification system, having a control apparatus as claimed in claim 1.

* * * * *